US007928083B2

(12) United States Patent
Hochberg

(10) Patent No.: US 7,928,083 B2
(45) Date of Patent: Apr. 19, 2011

(54) H19 SILENCING NUCLEIC ACID AGENTS FOR TREATING RHEUMATOID ARTHRITIS

(75) Inventor: Abraham Hochberg, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 12/523,288

(22) PCT Filed: Jan. 16, 2008

(86) PCT No.: PCT/IL2008/000071
§ 371 (c)(1),
(2), (4) Date: Dec. 3, 2009

(87) PCT Pub. No.: WO2008/087641
PCT Pub. Date: Jul. 24, 2008

(65) Prior Publication Data
US 2010/0105759 A1    Apr. 29, 2010

Related U.S. Application Data

(60) Provisional application No. 60/880,430, filed on Jan. 16, 2007, provisional application No. 60/880,425, filed on Jan. 16, 2007.

(51) Int. Cl.
A61K 31/70 (2006.01)
C07H 21/04 (2006.01)
(52) U.S. Cl. .................................. 514/44; 536/24.5
(58) Field of Classification Search .......................... None
See application file for complete search history.

(56) References Cited

U.S. PATENT DOCUMENTS

| | | | |
|---|---|---|---|
| 3,687,808 A | 8/1972 | Merigan, Jr. et al. | 195/28 |
| 3,791,932 A | 2/1974 | Schuurs et al. | 195/103.5 |
| 3,839,153 A | 10/1974 | Schuur et al. | 195/103.5 |
| 3,850,578 A | 11/1974 | McConnell | 23/230 |
| 3,850,752 A | 11/1974 | Schuur et al. | 195/103.5 |
| 3,853,987 A | 12/1974 | Dreyer | 424/1 |
| 3,867,517 A | 2/1975 | Ling | 424/1 |
| 3,879,262 A | 4/1975 | Schuur et al. | 195/63 |
| 3,901,654 A | 8/1975 | Gross | 23/230 |
| 3,935,074 A | 1/1976 | Rubenstein et al. | 195/103.5 |
| 3,984,533 A | 10/1976 | Uzgiris | 424/12 |
| 3,996,345 A | 12/1976 | Ullman et al. | 424/12 |
| 4,034,074 A | 7/1977 | Miles | 424/1 |
| 4,098,876 A | 7/1978 | Piasio et al. | 424/1 |
| 4,469,863 A | 9/1984 | Ts'o et al. | 536/27 |
| 4,476,301 A | 10/1984 | Imbach et al. | 536/27 |
| 4,666,828 A | 5/1987 | Gusella | 435/6 |
| 4,683,202 A | 7/1987 | Mullis | 435/91 |
| 4,801,531 A | 1/1989 | Frossard | 435/6 |
| 4,873,316 A | 10/1989 | Meade et al. | 530/412 |
| 4,879,219 A | 11/1989 | Wands et al. | 435/7 |
| 5,011,771 A | 4/1991 | Bellet et al. | 435/7.94 |
| 5,023,243 A | 6/1991 | Tullis | 514/44 |
| 5,034,506 A | 7/1991 | Summerton et al. | 528/391 |
| 5,166,315 A | 11/1992 | Summerton et al. | 528/406 |
| 5,177,196 A | 1/1993 | Meyer, Jr. et al. | 536/22.1 |
| 5,185,444 A | 2/1993 | Summerton et al. | 544/81 |
| 5,188,897 A | 2/1993 | Suhadolnik et al. | 428/402.2 |
| 5,192,659 A | 3/1993 | Simons | 435/6 |
| 5,214,134 A | 5/1993 | Weis et al. | 536/25.3 |
| 5,216,141 A | 6/1993 | Benner | 536/27.13 |
| 5,235,033 A | 8/1993 | Summerton et al. | 528/391 |
| 5,264,423 A | 11/1993 | Cohen et al. | 514/44 |
| 5,264,562 A | 11/1993 | Matteucci | 536/23.1 |
| 5,264,564 A | 11/1993 | Matteucci | 536/23.1 |
| 5,272,057 A | 12/1993 | Smulson et al. | 435/6 |
| 5,276,019 A | 1/1994 | Cohen et al. | 514/44 |
| 5,278,302 A | 1/1994 | Caruthers et al. | 536/24.5 |
| 5,281,521 A | 1/1994 | Trojanowski | 395/142 |
| 5,286,717 A | 2/1994 | Cohen et al. | 514/44 |
| 5,321,131 A | 6/1994 | Agrawal et al. | 536/25.34 |
| 5,399,676 A | 3/1995 | Froehler | 536/23.1 |
| 5,405,938 A | 4/1995 | Summerton et al. | 528/406 |
| 5,405,939 A | 4/1995 | Suhadolnik et al. | 530/44 |
| 5,434,257 A | 7/1995 | Matteucci et al. | 536/24.3 |
| 5,453,496 A | 9/1995 | Caruthers et al. | 536/24.5 |
| 5,455,233 A | 10/1995 | Spielvogel et al. | 514/44 |
| 5,464,764 A | 11/1995 | Capecchi et al. | 435/172.3 |
| 5,466,677 A | 11/1995 | Baxter et al. | 514/44 |
| 5,470,967 A | 11/1995 | Huie et al. | 536/24.3 |
| 5,476,925 A | 12/1995 | Letsinger et al. | 536/23.1 |
| 5,487,992 A | 1/1996 | Capecchi et al. | 435/172.3 |
| 5,489,677 A | 2/1996 | Sanghvi et al. | 536/22.1 |
| 5,519,126 A | 5/1996 | Hecht | 536/24.3 |

(Continued)

FOREIGN PATENT DOCUMENTS

EP    375408    6/1990

(Continued)

OTHER PUBLICATIONS

International Search Report Appln. No. PCT/IL06/00785.
International Search Report Appln. No. PCT/IL08/00072.
International Search Report Appln. No. PCT/IL08/00071.
U.S. Appl. No. 12/523,298, filed Jul. 15, 2009.
U.S. Appl. No. 12/015,325, filed Jan. 16, 2008.
U.S. Appl. No. 11/994,810, filed Jul. 8, 2008.
Ariel et al., 1994, Gynecol Oncol 53, 212-219.
Ariel et al., 2004, Mol Carcinog 41, 69-76.
Ayesh and Matouk et al., 2002, Mol Carcinog 35, 63-74.
Ayesh and Matouk et al., 2003, Mol Ther 7, 535-541.
Banerji et al., 1983, Cell 33, 729-740.
Beal, P. A. and Dervan, P.B., et al., 1991, Science 251, 1360-1363.
Bernstein et al., 2001, Nature 409, 363-366.

(Continued)

Primary Examiner — Tracy Vivlemore
(74) Attorney, Agent, or Firm — Winston & Strawn LLP

(57) ABSTRACT

The invention relates to the treatment of rheumatoid arthritis, particularly to the use of nucleic acid agents capable of silencing H19 for the treatment of rheumatoid arthritis. The invention provides methods for ameliorating rheumatoid arthritis and symptoms associated therewith, utilizing gene silencing oligonucleotides such as small interfering RNA (siRNA) agents directed to H19.

21 Claims, No Drawings

U.S. PATENT DOCUMENTS

| | | | |
|---|---|---|---|
| 5,536,821 A | 7/1996 | Agrawal et al. | 536/22.1 |
| 5,539,082 A | 7/1996 | Nielsen et al. | 530/300 |
| 5,541,306 A | 7/1996 | Agrawal et al. | 536/22.1 |
| 5,541,307 A | 7/1996 | Cook et al. | 536/23.1 |
| 5,550,111 A | 8/1996 | Suhadolnik et al. | 514/44 |
| 5,561,225 A | 10/1996 | Maddry et al. | 536/23.1 |
| 5,563,253 A | 10/1996 | Agrawal et al. | 536/22.1 |
| 5,571,799 A | 11/1996 | Tkachuk et al. | 514/47 |
| 5,587,361 A | 12/1996 | Cook et al. | 514/44 |
| 5,596,086 A | 1/1997 | Matteucci et al. | 536/22.1 |
| 5,602,240 A | 2/1997 | De Mesmaeker et al. | 536/22.1 |
| 5,608,046 A | 3/1997 | Cook et al. | 536/22.1 |
| 5,610,289 A | 3/1997 | Cook et al. | 536/25.34 |
| 5,618,704 A | 4/1997 | Sanghvi et al. | 435/91.5 |
| 5,623,070 A | 4/1997 | Cook et al. | 536/27.6 |
| 5,625,050 A | 4/1997 | Beaton et al. | 536/24.1 |
| 5,633,360 A | 5/1997 | Bischofberger et al. | 536/22.1 |
| 5,663,312 A | 9/1997 | Chaturvedula | 536/22.1 |
| 5,677,437 A | 10/1997 | Teng et al. | 536/23.1 |
| 5,677,439 A | 10/1997 | Weis et al. | 536/23.1 |
| 5,714,331 A | 2/1998 | Buchardt et al. | 435/6 |
| 5,719,262 A | 2/1998 | Buchardt et al. | 530/300 |
| 5,721,138 A | 2/1998 | Lawn | 435/325 |
| 5,955,273 A | 9/1999 | Hochberg et al. | 435/6 |
| 6,303,374 B1 | 10/2001 | Zhang et al. | 435/375 |
| 6,326,174 B1 | 12/2001 | Joyce et al. | 435/91.31 |
| 7,041,654 B2 | 5/2006 | Hochberg et al. | 514/44 |
| 2002/0123476 A1 | 9/2002 | Emanuele et al. | 514/44 |
| 2002/0128218 A1 | 9/2002 | Emanuele et al. | 514/44 |
| 2003/0014372 A1 | 1/2003 | Wheeler et al. | 705/71 |
| 2003/0017068 A1 | 1/2003 | Larrain et al. | 417/567 |
| 2003/0096980 A1 | 5/2003 | Froehler et al. | 536/23.1 |
| 2003/0143732 A1 | 7/2003 | Fosnaugh et al. | 435/325 |
| 2004/0259247 A1 | 12/2004 | Tuschl et al. | 425/6 |
| 2005/0118625 A1 | 6/2005 | Mounts | 535/375 |

FOREIGN PATENT DOCUMENTS

| | | |
|---|---|---|
| EP | 264166 | 4/1998 |
| WO | WO 9524503 | 9/1995 |
| WO | WO 98/34613 | 8/1998 |
| WO | WO 00/71707 A1 | 11/2000 |
| WO | 2004/031359 | 4/2004 |
| WO | WO 2004003159 | 4/2004 |
| WO | WO 2006119266 A2 * | 11/2006 |

OTHER PUBLICATIONS

N. Berteaux et al, "H19 mRNA-like non-coding RNA promotes breast cancer cell proliferation through positive control by E2F1", The Journal of Biological Chemistry, vol. 280, No. 33 Papers in Press, pp. 29625-29636 (2005).

Besch et al., 2002, J Biol Chem 277, 32473-79.
Blythe, N.L. et al., 1996, J Anat 188( Pt 1), 65-74.
Brannan et al., 1990, Mol Cell Biol 10, 28-36.
Brantl, 2002, Biochem Biophys Act 1575, 15-25.
Breaker, R.R. and Joyce G., 1995, Chemistry and Biology 2, 655-660.
Byrne et al., 1989, Proc Natl Acad Sci USA 86, 5473-5477.
Calame et al., 1988, Adv. Immunol. 43, 235-275.
Carbone, et al., 2003, Nucl Acid Res 31, 833-43.
Cooney, M. et al., 1988 Science 241, 456-459.
Cullen, 2002, Nat Immunol 3, 597-599.
Edlund et al., 1985, Science 230, 912-916.
Gilboa et al., 1986, Biotechniques 4(6), 504-512.
Graveel et al, 2001, Oncogene 20, 2704-2712.
Hammond et al., 2001, Nat Rev Gen 2, 110-119.
Hutvagner and Zamore, 2002, Curr Opin Genetics and Development 12, 225-232.
Kaplan, R., et al., 2003, Cancer Res 63, 1475-1482.
Khachigian, L.M., 2002, Curr Opin Mol Ther 4, 119-21.
Liang, C.Y., et al., 2004, Arch Virol 149, 51-60.
Lottin et al, 2002, Carcinogesis 23, 1885-1895.
Lottin et al, 2002, Oncogene 21, 1625-1631.
Maher III, L. J., et al., 1989, Science 245, 725-730.
Matouk et al., 2005, Cancer Therapy 3, 249-266.
Matouk et al., 2006, Hepatology 44(4 Supp. 1), 529A.
Matouk et al., 2007, PLoS ONE 2(9), e845.
Moser, H.E., et al., 1987, Science 238, 645-650.
Pinkert et al., 1987, Genes Dev 1, 268-277.
Puri et al., 2001, J Biol Chem 276, 28991-98.
Rachmilewitz et al, 1995, Oncogene 11, 863-870.
Rodesch et al, 1992, Obstet Gynecol 80, 283-285.
Santoro, S.W. & Joyce, G.F., 1997, Proc Natl Acad Sci USA 94, 4262-4266.
Seidman and Glazer, 2003, J Clin Invest 112, 487-94.
Sharp, 2001, Genes Dev 15, 485-90.
Soreq et al., 1974, J Mol Bio 88, 233-45.
Stuhlmuller et al, 2003, Am J Pathol 163, 901-911.
Tonkinson et al., 1996, Cancer Investigation 14(1), 54-65.
Tuschl, 2001, ChemBiochem 2, 239-245.
Vasquez et al., 1999, Nucl Acids Res 27, 1176-81.
Vuyisich and Beal, 2000, Nuc Acids Res 28, 2369-74.
Welch et al., 1998, Clin Diagn Virol 10, 163-71.
Welch et al., 1998, Cuff Opin Biotechnol 9, 486-96.
Winoto et al., 1989, EMBO J 8, 729-733.
Zabala, M. et al., 2004, Cancer Res 64(8), 2799-804.

* cited by examiner

SEQUENCE LISTING

```
<160> NUMBER OF SEQ ID NOS: 27

<210> SEQ ID NO 1
<211> LENGTH: 19
<212> TYPE: DNA
<213> ORGANISM: Artificial
<220> FEATURE:
<223> OTHER INFORMATION: synthetic oligonucleotide

<400> SEQUENCE: 1
uaagucauuu gcacugguu                                                19

<210> SEQ ID NO 2
<211> LENGTH: 19
<212> TYPE: DNA
<213> ORGANISM: Artificial
<220> FEATURE:
<223> OTHER INFORMATION: synthetic oligonucleotide

<400> SEQUENCE: 2
gcaggacaug acauggucc                                                19

<210> SEQ ID NO 3
<211> LENGTH: 19
<212> TYPE: DNA
<213> ORGANISM: Artificial
<220> FEATURE:
<223> OTHER INFORMATION: synthetic oligonucleotide

<400> SEQUENCE: 3
ccaacaucaa agacaccau                                                19

<210> SEQ ID NO 4
<211> LENGTH: 19
<212> TYPE: DNA
<213> ORGANISM: Artificial
<220> FEATURE:
<223> OTHER INFORMATION: synthetic oligonucleotide

<400> SEQUENCE: 4
ccaggcagaa agagcaaga                                                19

<210> SEQ ID NO 5
<211> LENGTH: 21
<212> TYPE: DNA
<213> ORGANISM: Artificial
<220> FEATURE:
<223> OTHER INFORMATION: synthetic oligonucleotide

<400> SEQUENCE: 5
uaagucauuu gcacugguut t                                             21

<210> SEQ ID NO 6
<211> LENGTH: 21
<212> TYPE: DNA
<213> ORGANISM: Artificial
<220> FEATURE:
<223> OTHER INFORMATION: synthetic oligonucleotide

<400> SEQUENCE: 6
gcaggacaug acauggucct t                                             21
```

```
<210> SEQ ID NO 7
<211> LENGTH: 21
<212> TYPE: DNA
<213> ORGANISM: Artificial
<220> FEATURE:
<223> OTHER INFORMATION: synthetic oligonucleotide

<400> SEQUENCE: 7
ccaacaucaa agacaccaut t                                              21

<210> SEQ ID NO 8
<211> LENGTH: 21
<212> TYPE: DNA
<213> ORGANISM: Artificial
<220> FEATURE:
<223> OTHER INFORMATION: synthetic oligonucleotide

<400> SEQUENCE: 8
ccaggcagaa agagcaagat t                                              21

<210> SEQ ID NO 9
<211> LENGTH: 21
<212> TYPE: DNA
<213> ORGANISM: Artificial
<220> FEATURE:
<223> OTHER INFORMATION: synthetic oligonucleotide

<400> SEQUENCE: 9
cuuacgcuga guacuucgat t                                              21

<210> SEQ ID NO 10
<211> LENGTH: 2322
<212> TYPE: DNA
<213> ORGANISM: Homo sapiens

<400> SEQUENCE: 10 gggaggggt  gggatgggtg  gggggtaacg  ggggaaactg  gggaagtggg  gaaccgaggg      60
gcaaccaggg  gaagatgggg  tgctggagga  gagcttgtgg  gagccaagga  gcaccttgga    120
catctggagt  ctggcaggag  tgatgacggg  tggaggggct  agctcgaggc  agggctggtg    180
gggcctgagg  ccagtgagga  gtgtggagta  ggcgcccagg  catcgtgcag  acagggcgac    240
atcagctggg  gacgatgggc  ctgagctagg  gctggaaaga  aggggagcc   aggcattcat    300 cccggtcact  tttggttaca  ggacgtggca  gctggttgga  cgaggggagc  tggtgggcag    360
ggtttgatcc  cagggcctgg  gcaacggagg  tgtagctggc  agcagcgggc  aggtgaggac    420
cccatctgcc  gggcaggtga  gtcccttccc  tccccaggcc  tcgcttcccc  agccttctga    480
aagaaggagg  tttaggggat  cgagggctgg  cggggagaag  cagacaccct  cccagcagag    540
gggcaggatg  ggggcaggag  agttagcaaa  ggtgacatct  tctcgggggg  agccgagact    600
gcgcaaggct  gggggggttat  gggcccgttc  caggcagaaa  gagcaagagg  gcagggaggg    660
agcacagggg  tggccagcgt  agggtccagc  acgtggggtg  gtaccccagg  cctgggtcag    720
acagggacat  ggcaggggac  acaggacaga  ggggtcccca  gctgccacct  cacccaccgc    780
aattcattta  gtagcaggca  caggggcagc  tccggcacgg  ctttctcagg  cctatgccgg    840
agcctcgagg  gctggagagc  gggaagacag  gcagtgctcg  gggagttgca  gcaggacgtc    900
accaggaggg  cgaagcggcc  acggagggg   ggccccggga  cattgcgcag  caaggaggct    960
gcaggggctc  ggcctgcggg  cgccggtccc  acgaggcact  gcggcccagg  gtctggtgcg   1020
gagagggccc  acagtggact  tggtgacgct  gtatgccctc  accgctcagc  ccctggggct   1080
```

```
ggcttggcag acagtacagc atccagggga gtcaagggca tggggcgaga ccagactagg    1140
cgaggcgggc ggggcggagt gaatgagctc tcaggaggga ggatggtgca ggcaggggtg    1200
aggagcgcag cgggcggcga gcgggaggca ctggcctcca gagcccgtgg ccaaggcggg    1260
cctcgcgggc ggcgacggag ccgggatcgg tgcctcagcg ttcgggctgg agacgaggcc    1320
aggtctccag ctggggtgga cgtgcccacc agctgccgaa ggccaagacg ccaggtccgg    1380
tggacgtgac aagcaggaca tgacatggtc cggtgtgacg gcgaggacag aggaggcgcg    1440
tccggccttc ctgaacacct taggctggtg gggctgcggc aagaagcggg tctgtttctt    1500
tacttcctcc acggagtcgg cacactatgg ctgccctctg ggctcccaga acccacaaca    1560
tgaaagaaat ggtgctaccc agctcaagcc tgggcctttg aatccggaca caaaaccctc    1620
tagcttggaa atgaatatgc tgcactttac aaccactgca ctacctgact caggaatcgg    1680
ctctggaagg tgaagctaga ggaaccagac ctcatcagcc caacatcaaa gacaccatcg    1740
gaacagcagc gcccgcagca cccacccccgc accggcgact ccatcttcat ggccaccccc    1800
tgcggcggac ggttgaccac cagccaccac atcatcccag agctgagctc ctccagcggg    1860
atgacgccgt ccccaccacc tccctcttct tcttttcat ccttctgtct ctttgtttct     1920
gagctttcct gtctttcctt ttttctgaga gattcaaagc ctccacgact ctgtttcccc    1980
cgtcccttct gaatttaatt tgcactaagt catttgcact ggttggagtt gtggagacgg    2040
ccttgagtct cagtacgagt gtgcgtgagt gtgagccacc ttggcaagtg cctgtgcagg    2100
gcccggccgc cctccatctg gccgggtga ctgggcgccg ctgtgtgcc cgaggcctca      2160 ccctgccctc gcctagtctg gaagctccga ccgacatcac ggagcagcct tcaagcattc    2220
cattacgccc catctcgctc tgtgcccctc cccaccaggg cttcagcagg agccctggac    2280
tcatcatcaa taaacactgt tacagcaaaa aaaaaaaaa aa                        2322

<210> SEQ ID NO 11
<211> LENGTH: 22
<212> TYPE: DNA
<213> ORGANISM: Artificial
<220> FEATURE:
<223> OTHER INFORMATION: synthetic oligonucleotide

<400> SEQUENCE: 11
gcaagcugac ccugaaguuc au                                               22

<210> SEQ ID NO 12
<211> LENGTH: 16
<212> TYPE: DNA
<213> ORGANISM: Artificial
<220> FEATURE:
<223> OTHER INFORMATION: synthetic oligonucleotide

<400> SEQUENCE: 12
ccggccttcc tgaaca                                                      16

<210> SEQ ID NO 13
<211> LENGTH: 21
<212> TYPE: DNA
<213> ORGANISM: Artificial
<220> FEATURE:
<223> OTHER INFORMATION: synthetic oligonucleotide

<400> SEQUENCE: 13
ttccgatggt gtctttgatg t                                                21
```

```
<210> SEQ ID NO 14
<211> LENGTH: 24
<212> TYPE: DNA
<213> ORGANISM: Artificial
<220> FEATURE:
<223> OTHER INFORMATION: synthetic oligonucleotide

<400> SEQUENCE: 14
ggctctccag aacatcatcc ctgc                                              24

<210> SEQ ID NO 15
<211> LENGTH: 24
<212> TYPE: DNA
<213> ORGANISM: Artificial
<220> FEATURE:
<223> OTHER INFORMATION: synthetic oligonucleotide

<400> SEQUENCE: 15
gggtgtcgct gttgaagtca gagg                                              24

<210> SEQ ID NO 16
<211> LENGTH: 25
<212> TYPE: DNA
<213> ORGANISM: Artificial
<220> FEATURE:
<223> OTHER INFORMATION: synthetic oligonucleotide

<400> SEQUENCE: 16
ccucuagcuu ggaaaugaau augcu                                             25

<210> SEQ ID NO 17
<211> LENGTH: 25
<212> TYPE: DNA
<213> ORGANISM: Artificial
<220> FEATURE:
<223> OTHER INFORMATION: synthetic oligonucleotide

<400> SEQUENCE: 17
ccugacucag gaaucggcuc uggaa                                             25

<210> SEQ ID NO 18
<211> LENGTH: 25
<212> TYPE: DNA
<213> ORGANISM: Artificial
<220> FEATURE:
<223> OTHER INFORMATION: synthetic oligonucleotide

<400> SEQUENCE: 18
cccaacauca aagacaccau cggaa                                             25

<210> SEQ ID NO 19
<211> LENGTH: 21
<212> TYPE: DNA
<213> ORGANISM: Artificial
<220> FEATURE:
<223> OTHER INFORMATION: synthetic oligonucleotide

<400> SEQUENCE: 19
caccgcaauu cauuuaguau u                                                 21

<210> SEQ ID NO 20
<211> LENGTH: 21
<212> TYPE: DNA
<213> ORGANISM: Artificial
<220> FEATURE:
<223> OTHER INFORMATION: synthetic oligonucleotide

<400> SEQUENCE: 20
```

-continued gaucggugcc ucagcguucu u                                           21

<210> SEQ ID NO 21
<211> LENGTH: 21
<212> TYPE: DNA
<213> ORGANISM: Artificial
<220> FEATURE:
<223> OTHER INFORMATION: synthetic oligonucleotide

<400> SEQUENCE: 21
uguaugcccu caccgcucau u                                           21

<210> SEQ ID NO 22
<211> LENGTH: 21
<212> TYPE: DNA
<213> ORGANISM: Artificial
<220> FEATURE:
<223> OTHER INFORMATION: synthetic oligonucleotide

<400> SEQUENCE: 22
ggagcagccu ucaagcauuu u                                           21

<210> SEQ ID NO 23
<211> LENGTH: 21
<212> TYPE: DNA
<213> ORGANISM: Artificial
<220> FEATURE:
<223> OTHER INFORMATION: synthetic oligonucleotide

<400> SEQUENCE: 23
ccacggaguc ggcacacuat t                                           21

<210> SEQ ID NO 24
<211> LENGTH: 21
<212> TYPE: DNA
<213> ORGANISM: Artificial
<220> FEATURE:
<223> OTHER INFORMATION: synthetic oligonucleotide

<400> SEQUENCE: 24
cagccuucaa gcauuccauu a                                           21

<210> SEQ ID NO 25
<211> LENGTH: 21
<212> TYPE: DNA
<213> ORGANISM: Artificial
<220> FEATURE:
<223> OTHER INFORMATION: synthetic oligonucleotide

<400> SEQUENCE: 25
cugcacuacc ugacucagga a                                           21

<210> SEQ ID NO 26
<211> LENGTH: 21
<212> TYPE: DNA
<213> ORGANISM: Artificial
<220> FEATURE:
<223> OTHER INFORMATION: synthetic oligonucleotide

<400> SEQUENCE: 26
cuccacggag ucggcacacu a                                           21

<210> SEQ ID NO 27
<211> LENGTH: 21
<212> TYPE: DNA
<213> ORGANISM: Artificial

```
-continued
<220> FEATURE:
<223> OTHER INFORMATION: synthetic oligonucleotide

<400> SEQUENCE: 27
ccucuagcuu ggaaaugaat t                                              21
```

H19 SILENCING NUCLEIC ACID AGENTS FOR TREATING RHEUMATOID ARTHRITIS

This application is a 371 filing of International Patent Application PCT/IL2008/000071 filed Jan. 16, 2008, which claims the benefit of application Nos. 60/880,425 and 60/880,430 both filed Jan. 16, 2007.

FIELD OF THE INVENTION

The invention is directed to compositions and methods for treating rheumatoid arthritis, utilizing H19-silencing nucleic acid agents.

BACKGROUND OF THE INVENTION

Rheumatoid arthritis (RA) is a chronic autoimmune disease characterized by progressive damage to the joints. Inflammation of peripheral joints occurs (e.g. in wrists and metacarpophalangeal joints) and often results in progressive destruction of articular structures, which is usually accompanied by systemic symptoms. RA affects about 1% of the population, with women affected 2 to 3 times more often than men. Onset may be at any age, most often between 35 and 50 years, although children or the elderly can be affected as well.

The disease is characterized by an abnormal growth of connective tissue in the joints, including synovial tissue. Damage has been shown to be mediated by cytokines, chemokines, and metalloproteases. The joints of chronic rheumatoid arthritis patients have marked growth of synovial cells, formation of a multilayer structure due to abnormal growth of the synovial cells (pannus formation), invasion of the synovial cells into cartilage tissue and bone tissue, vascularization toward the synovial tissue, and infiltration of inflammatory cells such as lymphocytes and macrophages. Mechanisms of onset of chronic rheumatoid arthritis have been reported to be based on such factors as heredity, bacterial infection and the contribution of various cytokines and growth factors, but the overall mechanism of onset has remained unclear.

Although attempts have been made to develop therapeutic agents for treating RA, there is at present no satisfactory cure for the disease. In addition, many of the therapeutic agents administered to alleviate pain and inflammation associated with the disease, such as disease-modifying anti-rheumatic drugs (DMARDs) and non-steroidal anti-inflammatory agents (NSAIDs), produce intolerable side effects.

NSAIDs are of some help for alleviating the pain of RA but do not prevent erosions or disease progression. NSAIDs can cause peptic ulcer disease and gastrointestinal bleeding. Other possible adverse effects include headache, confusion and other neurological symptoms, worsening of hypertension, edema, and decreased platelet adhesiveness. Cyclooxygenase-2 (COX-2) inhibitors, or coxibs (e.g., celecoxib), appear to have efficacy comparable to nonselective NSAIDs and are less likely to cause gastrointestinal toxicity. However, recent evidence indicates that some, if not all, coxibs increase the risk of cardiovascular events (e.g. stroke) with long-term use.

Disease-modifying anti-rheumatic drugs (DMARDs) appear to slow the progression of RA and are indicated in nearly all patients with RA. About ⅔ of patients improve overall, but complete remissions are uncommon. They have minimal immediate analgesic effects, so NSAIDs must often be continued. Examples of DMARDs include methotrexate, hydroxychloroquine, sulfasalazine, parenteral gold compounds, and oral penicillamine.

Systemic corticosteroids decrease symptoms more rapidly and to a greater degree than other drugs. However, they do not prevent joint destruction, and their clinical benefit often diminishes with time. Furthermore, severe rebound follows the withdrawal of corticosteroids in active disease. Because of their long-term adverse effects, many doctors recommend that corticosteroids be given to maintain function only until another DMARD has taken effect.

Cytotoxic or immunosuppressive drugs (e.g. azathioprine, cyclosporine and cyclophosphamide) provides efficacy similar to DMARDs. However, immunosuppressants are more toxic, particularly cyclophosphamide, which can cause bone marrow suppression and increase risk of cancer. Thus, these drugs are used only for patients in whom treatment with DMARDs has failed or to decrease the need for corticosteroids.

Other agents, such as interleukin-1 (IL-1) receptor antagonists and TNF-α antagonists, are also used for the treatment of RA in adults, often in combination with other treatments. Common side effects include cytopenia and infection.

However, the need remains for effective treatments useful for treating RA. Recently, attempts to develop specific nucleic acid agents (such as antisense and RNA interfering molecules) that may potentially be used in the therapy of RA have been reported. For example, PCT Pub. Nos. WO 2005/112971, WO 2005/079862, and WO 03/070897 disclose downregulating nucleic acid agents directed to proprotein convertase, resistin and TNF alpha, respectively. However, currently no nucleic acid based agent is in use for treating rheumatoid arthritis in humans.

Silencing Oligonucleic Acids

The silencing or down regulation of specific gene expression in a cell can be effected by oligonucleic acids using techniques known as antisense therapy, RNA interference (RNAi), and enzymatic nucleic acid molecules.

Antisense therapy refers to the process of inactivating target DNA or mRNA sequences through the use of complementary DNA or RNA oligonucleic acids, thereby inhibiting gene transcription or translation. An antisense molecule can be single stranded, double stranded or triple helix.

Other agents capable of inhibiting expression are for example enzymatic nucleic acid molecules such as DNAzymes and ribozymes, capable of specifically cleaving an mRNA transcript of interest. DNAzymes are single-stranded deoxyribonucleotides that are capable of cleaving both single- and double-stranded target sequences. Ribozymes are catalytic ribonucleic acid molecules that are increasingly being used for the sequence-specific inhibition of gene expression by the cleavage of mRNAs encoding proteins of interest.

RNA interference (hereinafter "RNAi") is a method of post-transcriptional inhibition of gene expression that is conserved throughout many eukaryotic organisms. RNAi is induced by short (i.e., <30 nucleotide) double stranded RNA ("dsRNA") molecules, which are present in the cell. These short dsRNA molecules, called "short interfering RNA" or "siRNA", cause the destruction of messenger RNAs ("mRNAs") that share sequence homology with the siRNA to within one nucleotide resolution. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

U.S. Pat. No. 6,506,559 to Fire et al. teaches genetic inhibition by double-stranded RNA, particularly a process for inhibition of gene expression of a target gene in a cell using RNA having a region with double-stranded structure, wherein the nucleotide sequences of the duplex region of the RNA and of a portion of the target gene are identical.

PCT Pub. No. WO 01/75164 to Tuschl et al. discloses that synthetic siRNA of 21 and 22 nucleotides in length, and which have short 3' overhangs, are able to induce RNAi of target mRNA in a Drosophila cell lysate. Cultured mammalian cells also exhibit RNAi degradation with synthetic siRNA. PCT Pub. No. WO 02/44321 relates to sequence and structural features of double-stranded (ds) RNA molecules required to mediate target-specific nucleic acid modifications such as RNA-interference and/or DNA methylation.

PCT Pub. No. WO 2006/060454 teaches methods of designing small interfering RNAs, antisense polynucleotides, and other hybridizing nucleotides. US Patent Application Publication No. 2006/0217331 discloses chemically modified double stranded nucleic acid molecules for RNA interference.

H19 and Use Thereof in Cancer Diagnosis and Therapy

H19 was the first human imprinted non protein-coding gene to be identified showing expression of only the maternal allele. It is also imprinted in mice. H19 was mapped on the short arm of the human chromosome 11, band 15.5, homologous to a region of murine chromosome 7. It belongs to a group of genes that very likely does not code for a protein product. H19 gene is abundantly expressed in embryogenesis but is shut off in most tissues after birth. However, studies of various tumors have demonstrated a re-expression or an overexpression of the H19 gene when compared to healthy tissues. Moreover in cancers of different etiologies and lineages, aberrant expression in allelic pattern was observed in some cases. While H19 shows mono-allelic expression in most tissues throughout development, with the exception of germ cells at certain stages of maturation, and in extra-villous trophoblasts, bi-allelic expression of this gene, referred as "relaxation of imprinting" or "loss of imprinting", have been found in an increasing number of cancers, for example, hepatocellular carcinoma, liver neoplasms, lung adenocarcinoma, esophageal, ovarian, rhabdomyosarcoma, cervical, bladder, head and neck squamous cell carcinoma, colorectal, uterus and in testicular germ cell tumors. Today nearly 30 types of cancers show dysregulated expression of H19 gene as compared to healthy tissues, with or without loss of imprinting.

Gene expression analyses using cancer cell lines have identified a plethora of downstream effectors of H19 RNA. Among these are group of genes that were previously reported to play crucial roles in some aspects of the tumorigenic process (Ayesh et al., 2002; Matouk et al., 2007; Lottin et al., 2002). H19 RNA presence may enhance the invasive, migratory and angiogenic capacity of the cell by up regulating genes that function in those pathways, and thus could contribute at least to the initial steps of the metastatic cascade. Additional studies highlight the potential role of H19 in promoting cancer progression and tumor metastasis by being a gene responsive to HGF/SF.

The specific expression of H19 gene in cancer cells has prompted its use in clinical applications for diagnosing cancer. For example, U.S. Pat. No. 5,955,273 to some of the inventors of the present invention teaches the use of H19 gene as a tumor specific marker. PCT Pub. No. WO 2004/024957 to some of the inventors of the present invention discloses the use of H19 for the detection, in a patient suspected of having cancer, of the presence of residual cancer cells or micrometastases originating from solid tumors.

PCT Pub. No. WO 99/18195 teaches the specific expression of heterologous sequences, particularly genes encoding cytotoxic products (e.g. Diphtheria toxin), in tumor cells under the control of cancer specific promoters (e.g., H19 promoter).

A publication by Stuhlmüller et al. (2003) discloses that H19 RNA is expressed in RA synovial tissue. The Stuhlmüller et al. publication demonstrates an increased expression of H19 in synovial fibroblasts grown in vitro under serum starvation conditions, and consequently postulates that H19 might have a pathogenic role in RA. According to Stuhlmüller et al., the pathophysiological role of H19 RNA remains elusive, and its particular role in RA awaits elucidation by functional studies and mutation analysis. Stuhlmüller et al. do not teach or suggest nucleic acid agents useful for treating RA.

PCT Pub. No. WO 04/031359 teaches a method for regulating the expression of angiogenesis-controlling genes in cells that are involved in neo-vascularization, comprising administering to the cells an effective amount of an H19 modulator. WO 04/031359 provides a list of angiogenesis-associated conditions, which purportedly may potentially be treated by either increasing or decreasing H19 expression, including, inter alia, RA. While a number of angiogenesis-associated genes were reported to be up-regulated in a carcinoma cell line transfected with an H19-expressing construct, down-regulation of H19 was not demonstrated. Specific and efficacious siRNA agents, capable of down-regulating H19, were neither taught nor suggested.

A publication by Berteaux et al. (2005) discloses two specific siRNA molecules targeted to H19, which arrest in vitro growth of breast cancer cells.

Additional species of siRNA intended for silencing H19 are now also available from commercial sources, including Invitrogen, Dharmacon and Qiagen. The efficacy of such commercially available H19 siRNA sequences is putative and their utility remains to be established. Certain commercially available molecules correspond to SEQ ID NOs: 14-25 of the present application.

WO 2007/034487 discloses a nucleic acid construct comprising: (i) a first nucleic acid sequence encoding TNF alpha; (ii) a second nucleic acid sequence encoding a Diphtheria toxin; and (iii) at least one additional nucleic acid sequence comprising a cancer specific promoter (e.g. an H19 promoter); the TNF alpha and Diphtheria toxin encoding sequences being under an expression control of the cancer specific promoter. Also provided are construct systems and methods and uses of same.

WO 2007/007317, published after the priority date of the present invention, discloses isolated oligonucleotides capable of down-regulating a level of H19 mRNA in cancer cells, corresponding to SEQ ID NOS: 5-8 of the present invention. Also disclosed are articles of manufacture comprising agents capable of downregulating H19 mRNA in combination with an additional anti-cancer treatment as well as methods of treating cancer by administering same.

None of the prior art discloses or suggests that nucleic acid agents that inhibit H19 expression may be applied effectively in rheumatoid arthritis therapy. There remains an unmet medical need for therapeutic modalities useful for treating rheumatoid arthritis and inhibiting symptoms associated therewith.

SUMMARY OF THE INVENTION

The invention provides compositions and methods useful for rheumatoid arthritis (RA) therapy, particularly nucleic acid agents capable of silencing or reducing the expression of the H19 gene for the treatment of RA. In particular, the invention is directed to novel therapeutic uses for H19-silencing oligonucleotides for the preparation of pharmaceutical compositions useful for inhibiting the progression of RA and ameliorating symptoms thereof.

While H19 RNA was reported to be expressed in RA synovial tissue, silencing of H19 has not previously been demonstrated to be beneficial for ameliorating the clinical signs of the disease or inhibiting its progression. Surprisingly, the present invention discloses that small interfering RNA (siRNA) agents directed to H19 exert a beneficial effect in experimental models of rheumatoid arthritis. It is further disclosed for the first time that these agents are useful for silencing H19 in non-malignant cells.

According to a first aspect, the invention provides methods for treating and preventing the progression of rheumatoid arthritis, utilizing H19-silencing oligonucleotides or recombinant constructs encoding them, as detailed herein.

H19-silencing oligonucleotides which may be used in the methods of the invention are those having a nucleic acid sequence asset forth in any one of SEQ ID NOS: 1-8 and 16-27, as detailed hereinbelow.

According to some embodiments, H19-silencing oligonucleotides of the invention comprise a nucleic acid sequence as set forth in any one of SEQ ID NOS: 1-4, and analogs and derivatives thereof, as follows:

```
UAAGUCAUUUGCACUGGUU;      (SEQ ID NO: 1)

GCAGGACAUGACAUGGUCC;      (SEQ ID NO: 2)

CCAACAUCAAAGACACCAU;      (SEQ ID NO: 3)
and

CCAGGCAGAAAGAGCAAGA.      (SEQ ID NO: 4)
```

In a preferable embodiment, the oligonucleotide is a small interfering RNA (siRNA) molecule, having a sense nucleic acid sequence as set forth in any one of SEQ ID NOS:1-4.

In certain embodiments, the siRNA molecules of the invention comprise a sense RNA strand and an antisense RNA strand, wherein the sense and the antisense RNA strands form an RNA duplex. Typically, each strand of the siRNA molecule is no more than 30 nucleotides in length, and is preferably about 20-25 or 21-23 nucleotides in length. The siRNA molecules may further comprise 3' nucleotide overhangs on either or both strands, i.e. terminal portions of the nucleotide sequence that are not base paired between the two strands of the double stranded siRNA molecule. Preferably, the overhang is about 1-5 nucleotides in length, more preferably 2 nucleotides in length.

In certain embodiments, said siRNA molecules comprise two 3' deoxythymidine overhangs, thus containing a sense strand having a nucleic acid sequence as set forth in any one of SEQ ID NOS: 5-8, as follows:

```
UAAGUCAUUUGCACUGGUUdTdT;    (SEQ ID NO: 5)

GCAGGACAUGACAUGGUCCdTdT;    (SEQ ID NO: 6)

CCAACAUCAAAGACACCAUdTdT;    (SEQ ID NO: 7)
and

CCAGGCAGAAAGAGCAAGAdTdT.    (SEQ ID NO: 8)
```

In another embodiment, said siRNA molecules comprise at least one modified internucleoside linkage. In a particular embodiment, said modified internucleoside linkage is a phosphorothioate linkage. For example, in certain particular embodiments, said siRNA molecule comprises one or two phosphorothioate linkages at the 3' termini of each strand.

In another embodiment, said siRNA molecules comprise at least one 2'-sugar modification. In a particular embodiment, said 2'-sugar modification is a 2'-O-methyl modification.

In another particular embodiment, said siRNA molecules comprise both modified internucleoside linkages (e.g. phosphorothioate linkages) and 2'-sugar modification (e.g. 2'-O-methyl modifications).

The methods of the invention are effected by administering to, or expressing in cells of the subject a therapeutically effective amount of at least one H19-silencing oligonucleotide of the invention, as detailed herein.

In one aspect, there is provided a method for treating or inhibiting the progression of rheumatoid arthritis in a subject in need thereof, comprising administering to the subject a therapeutically effective amount of at least one H19-silencing oligonucleotide of the invention.

In another aspect, there is provided a method for ameliorating or preventing the symptoms of rheumatoid arthritis in a subject in need thereof, comprising administering to the subject a therapeutically effective amount of at least one H19-silencing oligonucleotide of the invention.

In another aspect, there is provided a method for specifically reducing H19 expression in synovial tissue of a subject afflicted with rheumatoid arthritis, comprising administering to the subject a therapeutically effective amount of at least one H19-silencing oligonucleotide of the invention.

In some embodiments, the at least one H19-silencing oligonucleotide is administered to said subject in the form of a pharmaceutical composition further comprising a pharmaceutically acceptable carrier, excipient or diluent.

In another aspect, there is provided a method for treating or inhibiting the progression of rheumatoid arthritis in a subject in need thereof, comprising administering to the subject a therapeutically effective amount of at least one recombinant construct comprising a nucleic acid sequence encoding an H19-silencing oligonucleotide of the invention, the nucleic acid sequence being operably linked to at least one transcription regulating sequence.

In another aspect, there is provided a method for ameliorating or preventing the symptoms of rheumatoid arthritis in a subject in need thereof, comprising administering to the subject a therapeutically effective amount of at least one recombinant construct comprising a nucleic acid sequence encoding an H19-silencing oligonucleotide of the invention, the nucleic acid sequence being operably linked to at least one transcription regulating sequence.

According to yet a further aspect, there is provided a method for specifically reducing H19 expression in synovial tissue of a subject afflicted with rheumatoid arthritis, comprising administering to the subject a therapeutically effective amount of at least one recombinant construct comprising a nucleic acid sequence encoding an H19-silencing oligonucleotide of the invention, the nucleic acid sequence being operably linked to at least one transcription regulating sequence.

Other objects, features and advantages of the present invention will become clear from the following description.

DETAILED DESCRIPTION OF THE INVENTION

The present invention relates to the treatment of rheumatoid arthritis (RA), particularly to the use of nucleic acid agents capable of reducing, inhibiting, silencing or otherwise downregulating the expression of H19 RNA, for RA therapy. The invention provides methods for ameliorating RA and symptoms associated therewith, utilizing gene silencing oligonucleotides such as small interfering RNA (siRNA) agents directed to H19 and nucleic acid constructs encoding them.

Nucleic Acid Synthesis

The nucleic acid agents designed according to the teachings of the present invention can be generated according to any nucleic acid synthesis method known in the art, including both enzymatic syntheses or solid-phase syntheses, as well as using recombinant methods well known in the art.

Equipment and reagents for executing solid-phase synthesis are commercially available from, for example, Applied Biosystems. Any other means for such synthesis may also be employed; the actual synthesis of the nucleic acid agents is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; utilizing solid-phase chemistry, e.g. cyanoethyl phosphoramidite followed by deprotection, desalting, and purification by, for example, an automated trityl-on method or HPLC.

It will be appreciated that nucleic acid agents of the present invention can be also generated using an expression vector as is further described hereinbelow.

Optionally and preferably, the nucleic acid agents of the present invention are modified. Nucleic acid agents can be modified using various methods known in the art.

In certain embodiments, nucleic acid agents are modified either in backbone, internucleoside linkages, or bases, as is broadly described hereinunder.

Specific examples of nucleic acid agents useful according to this aspect of the present invention include oligonucleotides or polynucleotides containing modified backbones or non-natural internucleoside linkages. Examples of oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Other modified oligonucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other nucleic acid agents which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Nucleic acid agents of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), pages 858-859; Englisch et al. (1991); and Sanghvi (1993). Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

Silencing Oligonucleic Acids

The nucleic acid agents of the present invention are of at least 10, at least 15, or at least 17 bases specifically hybridizable with H19 RNA, but excluding the full length H19 RNA transcript or known variants thereof. The H19-silencing oligonucleotides of the invention are preferably no more than about 1000 bases in length, more preferably no more than about 100 bases in length. In other preferable embodiments, the oligonucleotides are no more than 30 nucleotides (or base pairs) in length.

The terms "oligonucleotide" and "oligonucleic acid" are used interchangeably and refer to an oligomer or polymer of ribonucleic acid (ribo-oligonucleotide or ribo-oligonucleoside) or deoxyribonucleic acid. These terms include nucleic acid strands composed of naturally occurring nucleobases, sugars and covalent intersugar linkages as well as oligonucleotides having non-naturally occurring portions which function similarly. Such modified or substituted oligonucleotides may be preferred over native forms because of the valuable characteristics including, for example, increased stability in the presence of plasma nucleases and enhanced cellular uptake.

The terms "H19-silencing oligonucleic acid", "H19 expression-inhibiting oligonucleic acid", "H19 expression-inhibiting oligonucleotide" or "oligonucleic acid that inhibits or reduces H19 expression" as used herein, denote an oligonucleic acid capable of specifically reducing the level or expression of the gene product, i.e. the level of H19 RNA, below the level that is observed in the absence of the oligonucleic acid. In some embodiments gene expression is downregulated by at least 25%, preferably at least 50%, at least 70%, 80% or at least 90%. Expression-inhibiting (downregulating or silencing) oligonucleic acids include, for example, RNA interfering molecules (RNAi) as detailed herein.

In some embodiments, certain commercially available H19-specific siRNA molecules are used in the methods of the invention, e.g. those having a nucleic acid sequence as denoted by SEQ ID NOs: 16-27, as follows:

```
                                     SEQ ID NO: 16
CCUCUAGCUUGGAAAUGAAUAUGCU (Exon 4, 1617-1641);

SEQ ID NO: 17
CCUGACUCAGGAAUCGGCUCUGGAA (Exon 4, 1664-1688);

SEQ ID NO: 18
CCCAACAUCAAAGACACCAUCGGAA (Exon 5, 1719-1743);

SEQ ID NO: 19
CACCGCAAUUCAUUUAGUAUU (Exon 1, 775-793);

SEQ ID NO: 20
GAUCGGUGCCUCAGCGUUCUU (Exon 1, 1285-1303);

SEQ ID NO: 21
UGUAUGCCCUCACCGCUCAUU (Exon 1, 1050-1068);

SEQ ID NO: 22
GGAGCAGCCUUCAAGCAUUUU (Exon 5, 2201-2219);

SEQ ID NO: 23
CCACGGAGUCGGCACACUAdTdT (Exon 1, 1509-1527);

SEQ ID NO: 24
CAGCCUUCAAGCAUUCCAUUA (Exon 5, 2205-2225);

SEQ ID NO: 25
CUGCACUACCUGACUCAGGAA (Exon 4, 1656-1676);

SEQ ID NO: 26
CUCCACGGAGUCGGCACACUA (Exon 3, 1507-1527);

SEQ ID NO: 27
CCUCUAGCUUGGAAAUGAAdTdT (1617-1635).
```

In certain embodiments, the siRNA comprises a sense strand as set forth in any one of SEQ ID NOS: 16-18. In certain other embodiments, the siRNA comprises a sense strand as set forth in any one of SEQ ID NOS: 20 and 22. In other particular embodiments, the siRNA comprises a sense strand as set forth in any one of SEQ ID NOS: 24-26.

As illustrated in Table 1 hereinbelow, preferable silencing oligonucleotides of the invention are targeted to (hybridizable with) specific areas of the H19 transcript identified in exons 1, 2, and 5, and substantially comprise a nucleic acid sequence as set forth in any one of SEQ ID NOS: 1-4:

TABLE 1 exemplary H19-downregulating sequences (sense strand)

| Sense sequence | Location | SEQ ID NO: |
|---|---|---|
| 5'-UAAGUCAUUUGCACUGGUU-3' | Exon 5 (2006-2024) | 1 |
| 5'-GCAGGACAUGACAUGGUCC-3' | Exon 2 (1393-1411) | 2 |
| 5'-CCAACAUCAAAGACACCAU-3' | Exon 5 (1720-1738) | 3 |
| 5'-CCAGGCAGAAAGAGCAAGA-3' | Exon 1 (630-648) | 4 |

In Table 1, the nucleotide positions are relative to H19 transcript as set forth in Accession No. NR_002196 (SEQ ID NO: 10).

In various embodiments, said oligonucleotide is selected from the group consisting of: an antisense molecule, a RNA interference (RNAi) molecule (e.g. small interfering RNAs (siRNAs) and hairpin RNAs) and an enzymatic nucleic acid molecule (e.g. ribozymes and DNAzymes), as detailed hereinbelow. In a preferable embodiment, the oligonucleotide is a siRNA molecule.

A small interfering RNA (siRNA) molecule is an example of a preferable nucleic acid agent capable of downregulating H19 RNA. RNA interference is a two-step process. During the first step, which is termed the initiation step, input dsRNA is digested into 21-23 nucleotide (nt) small interfering RNAs (siRNA), probably by the action of Dicer, a member of the RNase III family of dsRNA-specific ribonucleases, which cleaves dsRNA (introduced directly or via an expressing vector, cassette or virus) in an ATP-dependent manner. Successive cleavage events degrade the RNA to 19-21 by duplexes (siRNA), each strand with 2-nucleotide 3' overhangs.

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA. Although the mechanism of cleavage is still to be elucidated, research indicates that each RISC contains a single siRNA and an RNase.

It is possible to eliminate the "initiation step" by providing a priori siRNA. Because of the remarkable potency of RNAi, an amplification step within the RNAi pathway has been suggested. Amplification could occur by copying of the input dsRNAs, which would generate more siRNAs, or by replication of the siRNAs formed. Alternatively or additionally, amplification could be effected by multiple turnover events of the RISC. For more information on RNAi see the following reviews Tuschl (2001); Cullen (2002); and Brantl (2002).

Synthesis of RNAi molecules suitable for use with the present invention can be effected as follows. First, the H19 nucleic acid sequence target is optionally scanned downstream for AA dinucleotide sequences. Occurrence of each AA and the 3' adjacent 19 nucleotides is recorded as potential siRNA target sites.

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites that exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Thus, one currently preferred siRNA molecule of the invention comprises a sense strand and an antisense strand, the sense strand having a nucleic acid sequence as set forth in any one of SEQ ID NOS:1-4, wherein the sense and/or the antisense strand optionally comprises a 3' overhang. In one embodiment, the sense strand has a nucleic acid sequence as set forth in SEQ ID NO: 1. In another embodiment, the sense strand has a nucleic acid sequence as set forth in SEQ ID NO: 2. In another embodiment, the sense strand has a nucleic acid sequence as set forth in SEQ ID NO: 3. In another embodiment, the sense strand has a nucleic acid sequence as set forth in SEQ ID NO: 4. Each possibility represents a separate embodiment of the present invention.

The siRNA molecules of the invention comprise sense and antisense strands having nucleic acid sequence complementarity, wherein each strand is typically about 18-30 nucleotides in length. For example, each strand of the double stranded region may be e.g. 19-28, 19-26, 20-25 or 21-23 nucleotides in length.

In some embodiments, the sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

Preferably, one or both strands of the siRNA of the invention can also comprise a 3' overhang. As used herein, a "3' overhang" refers to at least one unpaired nucleotide extending from the 3'-end of an RNA strand. Thus in one embodiment, the siRNA of the invention comprises at least one 3' overhang of from 1 to about 6 nucleotides (which includes ribonucleotides or deoxynucleotides) in length, from 1 to about 5 nucleotides in length, from 1 to about 4 nucleotides in length, or from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid ("TT") or diuridylic acid ("UU").

As illustrated in Table 2 hereinbelow, exemplary siRNA oligonucleotides of the present invention are 19 base pairs in length with two 3' overhangs on each strand:

TABLE 2 exemplary siRNA sequences (sense strand)

| Sense sequence | SEQ ID NO: |
|---|---|
| 5'-UAAGUCAUUUGCACUGGUUdTdT-3' | 5 |
| 5'-GCAGGACAUGACAUGGUCCdTdT-3' | 6 |
| 5'-CCAACAUCAAAGACACCAUdTdT-3' | 7 |
| 5'-CCAGGCAGAAAGAGCAAGAdTdT-3' | 8 |

In one embodiment, the sense strand has a nucleic acid sequence as set forth in SEQ ID NO: 5. In another embodiment, the nucleic acid sequence of the sense strand is as set forth in SEQ ID NO: 5. In another embodiment, the sense strand has a nucleic acid sequence as set forth in SEQ ID NO: 6. In another embodiment, the nucleic acid sequence of the sense strand is as set forth in SEQ ID NO: 6. In another embodiment, the sense strand has a nucleic acid sequence as set forth in SEQ ID NO: 7. In another embodiment, the nucleic acid sequence of the sense strand is as set forth in SEQ ID NO7. In another embodiment, the sense strand has a nucleic acid sequence as set forth in SEQ ID NO: 8. In another embodiment, the nucleic acid sequence of the sense strand is as set forth in SEQ ID NO: 8. Each possibility represents a separate embodiment of the present invention.

While a preferable embodiment of the invention is directed to double-stranded siRNA molecules wherein the two 3' nucleotides are deoxythymidine residues, as illustrated in Table 2, it is to be understood that other modifications are within the scope of the present invention. Thus, the use of analogs, variants and derivatives of the sequences set forth in any one of SEQ ID NOS: 1-8 and 16-27 is contemplated, as long as the inhibitory activity of the H19-downregulating oligonucleotide is retained. For example, in a particular embodiment, the siRNA may contain 2'-O-methyl and/or phosphorothioate substituent nucleotides. In other particular embodiments, the siRNA is a variant, homolog or derivative of any one of SEQ ID NOs: 1-8 and 16-27.

As used herein, the term "variant" refers to substantially similar sequences possessing common qualitative biological activities. An oligonucleotide variant includes a pharmaceutically acceptable salt, homolog, analog, extension or fragment of a nucleotide sequence useful for the invention. Encompassed within the term "variant" are chemically modified natural and synthetic nucleotide molecules (derivatives). Also encompassed within the term "variant" are substitutions, additions or deletions within the nucleotide sequence of the molecule, as long as the required function is sufficiently maintained. Oligonucleotide variants may share at least 50%, 55%, 60%, 65%, 70%, 75%, 80%, 85%, 90%, 95%, 96%, 97%, 98% or 99% sequence identity (homology). In different embodiments, "homolog" may refer e.g. to any degree of homology disclosed herein.

In another aspect, the invention provides an H19-silencing oligonucleotide having a nucleic acid sequence as set forth in any one of SEQ ID NOS: 1-8, the oligonucleotide being no more than about 30 base pairs in length, comprising at least one phosphorothioate linkage and/or at least one 2'-O-methyl modification.

Another agent capable of silencing the expression of a H19 RNA is a DNAzyme molecule capable of specifically cleaving its encoding polynucleotides. DNAzymes are single-stranded nucleic acid agents which are capable of cleaving both single and double stranded target sequences. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (for a review of DNAzymes see Khachigian, 2002).

Examples of construction and amplification of synthetic, engineered DNAzymes recognizing single and double-stranded target cleavage sites have been disclosed in U.S. Pat. No. 6,326,174 to Joyce et al.

Another agent capable of silencing H19 is a ribozyme molecule capable of specifically cleaving its encoding polynucleotides. Ribozymes are being increasingly used for the sequence-specific inhibition of gene expression by the cleavage of mRNAs encoding proteins of interest (Welch et al., 1998). The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—http://www.rpi.com/index.html).

An additional method of silencing H19 is via triplex forming oligonucleotides (TFOs). In the last decade, studies have shown that TFOs can be designed which can recognize and bind to polypurine/polypirimidine regions in double-stranded helical DNA in a sequence-specific manner. Thus the DNA sequence encoding the H19 RNA of the present invention can be targeted thereby down-regulating the RNA molecule.

The recognition rules governing TFOs are outlined e.g. by EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, 2003).

In general, the triplex-forming oligonucleotide has the sequence correspondence:

```
oligo      3'--A      G      G      T duplex     5'--A      G      C      T duplex     3'--T      C      G      A
```

However, it has been shown that the A-AT and G-GC triplets have the greatest triple helical stability. The same authors have demonstrated that TFOs designed according to the A-AT and G-GC rule do not form non-specific triplexes, indicating that the triplex formation is indeed sequence specific.

Thus for any given sequence in the regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and subsequent formation of the triple helical structure with the target DNA, induces steric and functional changes, blocking transcription initiation and elongation, allowing the introduction of desired sequence changes in the endogenous DNA and results in the specific downregulation of gene expression. In addition, Vuyisich and Beal have recently shown that sequence specific TFOs can bind to dsRNA, inhibiting activity of dsRNA-dependent enzymes such as RNA-dependent kinases (Vuyisich and Beal, 2000). Additionally, TFOs designed according to the abovementioned principles can induce directed mutagenesis capable of effecting DNA repair, thus providing both downregulation and upregulation of expression of endogenous genes (Seidman and Glazer, 2003). Detailed description of the design, synthesis and administration of effective TFOs can be found in U.S. Patent Application Nos. 2003 017068 and 2003 0096980 to Froehler et al., and 2002 0128218 and 2002 0123476 to Emanuele et al., and U.S. Pat. No. 5,721,138 to Lawn.

It will be appreciated that nucleic acid agents capable of hybridizing H19 RNA may down-regulate an activity thereof by preventing H19 RNA binding to another downstream agent.

Recombinant Constructs

As mentioned hereinabove, the nucleic acid agents of the present invention (e.g., an siRNA molecule such as those set forth by any one of SEQ ID NOs:1-8) can be expressed in cells.

It will be appreciated that the agents of the present invention may be expressed directly in the subject (i.e. in vivo gene therapy) or may be expressed ex vivo in a cell system (autologous or non-autologous) and then administered to the subject.

To express such an agent (i.e., to produce an RNA molecule) in mammalian cells, a nucleic acid sequence encoding the agents of the present invention is preferably ligated into a nucleic acid construct suitable for mammalian cell expression. Such a nucleic acid construct includes a promoter sequence for directing transcription of the polynucleotide sequence in the cell in a constitutive or inducible manner.

The constructs of the present invention may be produced using standard recombinant and synthetic methods well known in the art. An isolated nucleic acid sequence can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis (see e.g. Sambrook et al., 2001; Ausubel, et al., 1989, Chapters 2 and 4). Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional oligonucleotide of the invention.

A nucleic acid molecule homolog can be produced using a number of methods known to those skilled in the art (see, for example, Sambrook et al., 2001). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. For example, nucleic acid molecule homologs can be selected from a mixture of modified nucleic acids by screening for the function of the oligonucleic acid encoded by the nucleic acid with respect to tumor progression, for example by the methods described herein.

The phrase "operably linked" refers to linking a nucleic acid sequence to a transcription control sequence in a manner such that the molecule is able to be expressed when transfected (i.e., transformed, transduced, infected or transfected) into a host cell. Transcription control sequences are sequences, which control the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Exemplary suitable transcription control sequences include those that function in animal, bacteria, helminth, yeast and insect cells. Preferably, the constructs of the invention comprise mammalian transcription control sequences, more preferably human regulatory sequences, and, optionally and additionally, other regulatory sequences.

Constitutive promoters suitable for use with the present invention are promoter sequences that are active under most environmental conditions and most types of cells such as the cytomegalovirus (CMV) and Rous sarcoma virus (RSV). Inducible promoters suitable for use with the present invention include for example the tetracycline-inducible promoter.

The nucleic acid construct (also referred to herein as an "expression vector") of the present invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the present invention is active in the specific cell population transformed. For example, without limitation, the construct may comprise TNF-alpha-specific regulatory sequences and/or H19-specific regulatory sequences such as the upstream H19 promoter region and the downstream H19 enhancer region. In certain embodiments, H19 promoter and enhancer sequences which can be used in accordance with the present invention include, but are not limited to, those described in U.S. Pat. No. 6,306,833. Yet in other particular embodiments, the silencing oligonucleic acids are under expression control of a promoter other than a H19 promoter.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase RNA stability.

Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The type of vector may be selected e.g. for producing single-stranded or double-stranded RNA or DNA. Suitable vectors for producing various silencing oligonucleic acids are known in the art. For example, RNAi expression vectors (also referred to as a dsRNA-encoding plasmid) are replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

Some of these vectors have been engineered to express small hairpin RNAs (shRNAs), which get processed in vivo into siRNA-like molecules capable of carrying out gene-specific silencing. Another type of siRNA expression vector encodes the sense and antisense siRNA strands under control of separate pol III promoters. The siRNA strands from this vector, like the shRNAs of the other vectors, have 3' thymidine termination signals. Silencing efficacy by both types of expression vectors was comparable to that induced by transiently transfecting siRNA.

Expression vectors containing regulatory elements from eukaryotic viruses such as retroviruses can be also used.

Various vectors for delivering and expressing silencing RNA molecules such as siRNAs are known in the art, and include for example plasmid vectors, inducible vectors, adenoviral vectors, retroviral vectors and lentiviral vectors and CMV-based vectors. Exemplary vectors include pSilencer™ vectors (Ambion), Genescript siRNA vectors, Imagenex vectors (e.g. IMG-1000, IMG-700 and IMG-1200), among others.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein.

Recombinant viral vectors are useful for in vivo expression of the H19-silencing agents of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into cells. Such methods are generally described in Sambrook et al, (1989, 1992), in Ausubel et al., (1989), Chang et al., (1995), Vega et al., (1995), and Gilboa et al. (1986), and include, for example, stable or transient transfection, lipofection, electroporation and infection with recombinant viral vectors. In addition, see U.S. Pat. Nos. 5,464,764 and 5,487,992 for positive-negative selection methods.

Useful lipids for lipid-mediated transfer of the gene are, for example, DOTMA, DOPE, and DC-Chol (Tonkinson et al., 1996). Other vectors can be used, such as cationic lipids, polylysine, and dendrimers.

Other than containing the necessary elements for the transcription of the inserted coding sequence, the expression construct of the present invention can also include sequences engineered to enhance stability, production, purification, yield or toxicity of the expressed RNA.

RA Symptoms and Signs

In certain embodiments, the H19-silencing oligonucleotides of the invention are useful for inhibiting, reducing or ameliorating the clinical symptoms and signs of RA.

The onset of RA is usually insidious, beginning with systemic symptoms and progressing to joint symptoms, but symptoms can occur simultaneously. Systemic symptoms include early morning stiffness of affected joints, generalized afternoon fatigue and malaise, anorexia, generalized weakness, and low-grade fever. Joint symptoms include pain and stiffness.

Joint symptoms are characteristically symmetric. Typically, stiffness lasts >60 min on rising in the morning but may occur after any prolonged inactivity. Involved joints become quite tender, with erythema, warmth, swelling, and limitation of motion. The wrists and the index and middle metacarpophalangeal joints are most commonly involved. Others include the proximal interphalangeal, metatarsophalangeal, elbows, and ankles; however, any joint may be involved. The axial skeleton is rarely involved except for the upper cervical spine. Synovial thickening is detectable. Joints are often held in flexion to minimize pain, which results from joint capsular distention.

Fixed deformities, particularly flexion contractures, may develop rapidly; ulnar deviation of the fingers with an ulnar slippage of the extensor tendons off the metacarpophalangeal joints is typical, as are swan-neck and boutonnière deformities. Joint instability can also occur. Carpal tunnel syndrome can result from wrist synovitis pressing on the median nerve. Ruptured popliteal (Baker's) cysts can develop, producing calf swelling and tenderness suggestive of deep venous thrombosis.

Subcutaneous rheumatoid nodules are not usually an early sign but eventually develop in up to 30% of patients, usually at sites of pressure and chronic irritation (e.g., the extensor surface of the forearm). Visceral nodules, usually asymptomatic, are common in severe RA. Other extra-articular signs include vasculitis causing leg ulcers or mononeuritis multiplex, pleural or pericardial effusions, pulmonary nodules, pulmonary fibrosis, pericarditis, myocarditis, lymphadenopathy, Felty's syndrome, Sjógren's syndrome, and episcleritis. Involvement of the cervical spine can produce atlantoaxial subluxation and spinal cord compression; it may worsen with extension of the neck (e.g., during endotracheal intubation).

The course of RA is unpredictable. The disease progresses most rapidly during the first 6 years, particularly the first year; 80% of patients develop some permanent joint abnormalities within 10 years.

Pharmaceutical Compositions

The agents of the present invention can be administered to a subject per se, or in a pharmaceutical composition where they are mixed with suitable carriers or excipients.

In various embodiments, the composition comprises as an active agent an H19-silencing oligonucleotide of the invention. It should further be noted, that H19 silencing agents (e.g. siRNA) used in the compositions and methods of the present invention may contain a nucleic acid sequence as denoted herein, including analogs, variants and derivatives thereof as detailed herein, with or without a 3' overhang. In certain embodiments, H19-silencing oligonucleotides (e.g. siRNA) having a nucleic acid sequence as set forth in any one of SEQ ID NOs: 1-8 and 16-27, including variants, analogs and derivatives thereof, may be used. Thus, for example, sequences in which a deoxythymidine residue has been substituted for a uracil residue or is absent may be used (for example, when expressing an siRNA molecule from a nucleic acid construct of the invention).

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the anti-RA effect (H19-silencing agent).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, or intranasal injections.

Alternately, one may administer the pharmaceutical composition in a local rather than systemic manner, for example, by intra-articular injections or by microinjections, under arthroscopy, into the inflammatory synovial tissue (i.e. in situ).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain thrmulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Preferably the pharmaceutical composition can also include a transfection agent such as DOTMA, DOPE, and DC-Chol (Tonkinson et al., 1996). A preferred example of a transfection agent is poly(ethylamine) (PEI).

Pharmaceutical compositions suitable for use in context of the present invention include compositions wherein the active ingredients are contained in an amount effective to achieve the intended purpose. More specifically, a therapeutically effective amount means an amount of active ingredients (nucleic acid agent) effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975).

Dosage amount and interval may be adjusted individually to provide plasma levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Therapeutic Use

According to various embodiments, the H19-silencing oligonucleotides of the invention are useful in RA therapy. Thus, the invention is directed to the use of a H19-silencing oligonucleotide of the invention for the preparation of a medicament useful for treating rheumatoid arthritis, for inhibiting the progression thereof, for ameliorating or preventing the symptoms associated therewith and/or for specifically reducing H19 expression in synovial tissue of a subject afflicted with rheumatoid arthritis as detailed herein.

In other embodiments the invention is directed to the use of a recombinant construct encoding an H19-silencing oligonucleotide of the invention for the preparation of a medicament useful for treating rheumatoid arthritis, for inhibiting the progression thereof, for ameliorating or preventing the symptoms associated therewith and/or for specifically reducing H19 expression in synovial tissue of a subject afflicted with rheumatoid arthritis as detailed herein.

In various embodiments, the H19-silencing oligonucleotide is specifically hybridizable with an H19 RNA comprising a sequence according to any one of SEQ ID NOS: 1-8 and 16-27.

In various embodiments, the H19-silencing oligonucleotide is a siRNA comprising a nucleic acid sequence as set forth in any one of SEQ ID NOs: 1-8 and 16-27, wherein each possibility represents a separate embodiment of the present invention. In other embodiments, said siRNA consists of a nucleic acid sequence as set forth in any one of SEQ ID NOs: 1-8 and 16-27, wherein each possibility represents a separate embodiment of the present invention. In other embodiments, said siRNA is a homolog, variant, fragment or variant of a fragment of these sequences as detailed herein, wherein each possibility represents a separate embodiment of the present invention.

In one aspect, there is provided a method for treating rheumatoid arthritis in a subject in need thereof, comprising administering to, or expressing in cells of the subject a therapeutically effective amount of at least one H19-silencing oligonucleotide having a nucleic acid sequence as set forth in any one of SEQ ID NOS: 1-4.

In another aspect, there is provided a method for inhibiting the progression of rheumatoid arthritis in a subject in need thereof, comprising administering to, or expressing in cells of the subject a therapeutically effective amount of at least one H19-silencing oligonucleotide having a nucleic acid sequence as set forth in any one of SEQ ID NOS: 1-4.

In another aspect, there is provided a method for ameliorating or preventing the symptoms of rheumatoid arthritis in a subject in need thereof, comprising administering to, or expressing in cells of the subject a therapeutically effective amount of at least one H19-silencing oligonucleotide having a nucleic acid sequence as set forth in any one of SEQ ID NOS: 1-4.

In another aspect, there is provided a method for specifically reducing H19 expression in synovial tissue of a subject afflicted with rheumatoid arthritis, comprising administering to, or expressing in cells of the subject a therapeutically effective amount of at least one H19-silencing oligonucleotide having a nucleic acid sequence as set forth in any one of SEQ ID NOS: 1-4.

In another aspect, the invention provides a pharmaceutical composition comprising a H19-silencing oligonucleotide having a nucleic acid sequence as set forth in any one of SEQ ID NOS: 1-4 for treating rheumatoid arthritis.

In another aspect, the invention provides a pharmaceutical composition comprising a H19-silencing oligonucleotide having a nucleic acid sequence as set forth in any one of SEQ ID NOS: 1-4 for inhibiting the progression of rheumatoid arthritis in a subject in need thereof.

In another aspect, the invention provides a pharmaceutical composition comprising a H19-silencing oligonucleotide having a nucleic acid sequence as set forth in any one of SEQ ID NOS: 1-4 for ameliorating or preventing the symptoms of rheumatoid arthritis.

In another aspect, the invention provides a pharmaceutical composition comprising a H19-silencing oligonucleotide having a nucleic acid sequence as set forth in any one of SEQ ID NOS: 1-4 for specifically reducing H19 expression in synovial tissue of a subject afflicted with rheumatoid arthritis.

In one embodiment, the at least one H19-silencing oligonucleotide is a small interference RNA (siRNA) molecule.

In another embodiment, the siRNA molecule comprises a sense RNA strand and an antisense RNA strand wherein the sense and the antisense RNA strands form an RNA duplex, and wherein at least one strand comprises a 3' overhang.

In another embodiment, the overhang is about 1-5 nucleotides in length.

In a particular embodiment, the overhang is 2 nucleotides in length.

In another embodiment, said siRNA molecule comprises a sense strand selected from the group consisting of SEQ ID NOS: 5-8.

In another embodiment, said siRNA molecule comprises at least one modified internucleoside linkage. In a particular embodiment, the modified internucleoside linkage is a phosphorothioate linkage.

In another embodiment, said siRNA molecule comprises at least one 2'-sugar modification. Thus, in certain embodiments, RNA analogs comprising substitutions for the hydroxyl group on the 2'-carbon atom of the ribose ring (e.g. 2'-O-methyl RNA, 2'-O-methoxyethyl (2'-MOE) RNA and 2'-fluoro RNA) may be used. In a particular embodiment, the 2'-sugar modification is a 2'-O-methyl modification.

In one aspect, there is provided a method for treating rheumatoid arthritis in a subject in need thereof, comprising administering to, or expressing in cells of the subject a therapeutically effective amount of at least one H19-silencing oligonucleotide having a nucleic acid sequence as set forth in any one of SEQ ID NOS: 16-27.

In another aspect, there is provided a method for inhibiting the progression of rheumatoid arthritis in a subject in need thereof, comprising administering to, or expressing in cells of the subject a therapeutically effective amount of at least one H19-silencing oligonucleotide having a nucleic acid sequence as set forth in any one of SEQ ID NOS: 16-27.

In another aspect, there is provided a method for ameliorating or preventing the symptoms of rheumatoid arthritis in a subject in need thereof, comprising administering to, or expressing in cells of the subject a therapeutically effective amount of at least one H19-silencing oligonucleotide having a nucleic acid sequence as set forth in any one of SEQ ID NOS: 16-27.

In another aspect, there is provided a method for specifically reducing H19 expression in synovial tissue of a subject afflicted with rheumatoid arthritis, comprising administering to, or expressing in cells of the subject a therapeutically effective amount of at least one H19-silencing oligonucleotide having a nucleic acid sequence as set forth in any one of SEQ ID NOS: 16-27.

In another aspect, the invention provides a pharmaceutical composition comprising a H19-silencing oligonucleotide having a nucleic acid sequence as set forth in any one of SEQ ID NOS: 16-27 for treating rheumatoid arthritis.

In another aspect, the invention provides a pharmaceutical composition comprising a H19-silencing oligonucleotide having a nucleic acid sequence as set forth in any one of SEQ ID NOS: 16-27 for inhibiting the progression of rheumatoid arthritis in a subject in need thereof.

In another aspect, the invention provides a pharmaceutical composition comprising a H19-silencing oligonucleotide having a nucleic acid sequence as set forth in any one of SEQ ID NOS: 16-27 for ameliorating or preventing the symptoms of rheumatoid arthritis.

In another aspect, the invention provides a pharmaceutical composition comprising a H19-silencing oligonucleotide having a nucleic acid sequence as set forth in any one of SEQ ID NOS: 16-27 for specifically reducing H19 expression in synovial tissue of a subject afflicted with rheumatoid arthritis.

In another embodiment, the at least one H19-silencing oligonucleotide (or recombinant construct encoding same) is administered to said subject in the form of a pharmaceutical composition further comprising a pharmaceutically acceptable carrier, excipient or diluent.

Preferably, the subject is human.

Advantageously, the at least one H19-silencing oligonucleotide (or recombinant construct encoding same) may be administered to said subject locally, e.g. by intra-articular injections or by microinjections, under arthroscopy, into the inflammatory synovial tissue.

The compositions of the invention can be administered alone or in conjunction with other therapeutic modalities. It is appropriate to administer the pharmaceutical compositions of the invention as part of a treatment regimen involving other therapies, such as drug therapy, which comprises e.g. DMARDs, NSAIDs and/or other agents used for the treatment of RA as known in the art.

The following examples are presented in order to more fully illustrate some embodiments of the invention. They should, in no way be construed, however, as limiting the broad scope of the invention.

EXAMPLES

Example 1

Preparation of siRNAs Targeting the H19 mRNA

Four siRNAs targeting human H19 RNA (SEQ ID NOs: 5-8, Table 2) and two negative control siRNAs (targeting luciferase pGL3, or GFP) were synthesized as ready-to-use duplexes by (Invitrogen U.S.A). All sequences were evaluated for gene specificity using the National Institutes of Health Blast program. The freeze-dried siRNAs were dissolved in Rnase-free water and stored as aliquots at 80° C.

The nucleic acid sequences of the control siRNAs (sense strand) are:

```
PGL3 siRNA (exon 1):
5'-CUUACGCUGAGUACUUCGAdTdT-3';    (SEQ ID NO: 9)

GFP siRNA (exon 1):
5'-GCAAGCUGACCCUGAAGUUCAU-3'.     (SEQ ID NO: 11)
```

Example 2

Inhibition of Expression of H19 and Downstream Effectors in Fibroblast Like Synoviocyte (FLS) by Using H19 siRNAs Fibroblast-like synoviocytes (FLS) are tested for expression of H19 and effector proteins following transfection with H19 siRNAs or control siRNAs, as detailed herein.

2.1 Cultivation of FLS

Synovial membranes collected from arthritic patients undergoing arthroplasty replacement, are cut to 2-3 mm pieces, submerged in 9 ml of PBS, and incubated with collagenase (1% type II collagenase, Sigma Chem. Co., USA) at 37° C. for 4 hrs, 5% (v/v) $CO_2$ gas. Then, 5 ml of DMEM medium (GIOBCO/Invitrogen, USA, 10% (v/v) fetal bovine serum, penicillin 100 unit/ml, and streptomycin 100 µg/ml) is added to inhibit collagenase activity, and the samples are centrifuged to harvest the cells. The cells thus collected are added to 15 ml of DMEM medium, and are cultured at 37° C. for 1 day under an environment of 5% (v/v) CO2 gas. Then, the cells attached on the bottom of culture container are collected and cultured again in DMEM medium under the same condition as specified above. Next, subcultures are performed repetitively to obtain fibroblast-like synoviocytes at passage(s) 3-6.

2.2 Transfection of Fibroblast-Like Synoviocyte with H19 siRNAs

Appropriate numbers of FLS cells obtained in 2.1 are cultured in 12-well plates under the same conditions. Transfection of siRNAs as detailed in Example 1 is conducted with lipofectamine 2000 (Invitrogen, U.S.A.) in 12 well plates. In some experiments, the cells are transfected with siRNAs corresponding to either SEQ ID NO: 4 or SEQ ID NO: 6. The day prior to transfection, the cells are trypsinized, counted, and seeded at 60,000 cells/well containing 1 ml DMEM medium without antibiotics so that they were nearly at 50% confluence on the day of transfection. Lipofectamine 2000 (3 µl) is incubated for 15 minutes with 100 µl serum-free OPTI-MEM medium (Invitro-gen, U.S.A.) and is supplemented with 50 pmoles dsRNA diluted in 100 µl serum-free OPTI-MEM media; the formulation lasts for 20 minutes. 195 µl of the mixture is applied to the cells and is incubated for 24 hours without replacement of the medium. Hep3B cells are then placed into an Aneoropack rectangular jar (Mitsubishi Chemical Company, Japan) and are supplemented with BBL GasPak Plus (Becton Dickson, Cock-eysville, Md., U.S.A.) to create hypoxic conditions within an hour. The progression of the hypoxic environment is monitored by a hypoxic indicator. Incubation lasts for an additional 24 hours before RNA extraction.

2.3. Measurement of mRNA Levels of H19 and Effector Proteins

Total cellular RNA is extracted from the FLS cells transfected with H19 siRNAs or GFP siRNA as a control (as in 2.2) after 24 and 48 hrs of transfection, using RNeasy mini kit (Qiagen, Germany). The mRNA levels of H19 and of downstream effectors of H19, such as p65 (relA), in total cellular RNA are measured using RT-PCR technique as follows.

1 µg total RNA is used to initiate cDNA synthesis using the p(dT)15 primer (Roche, Germany), with 400 units of Reverse Transcriptase (Gibco BRL), according to manufacturer's instructions. The PCR reaction for H19 is carried out using Taq polymerase (Takara, Otsu, Japan) for 29 cycles (94° C. for 30 s, 58° C. for 30 s, and 72° C. for 30 s) preceded by 94° C. for 5 min, and a final extension of 5 min at 72° C. PCR for GAPDH (control) is conducted as previously described (Ayesh et al., 2002; Matouk et al., 2007)

For downstream effectors the PCR conditions and PCR primers are optimized to check for differences in the expression levels that are affected by H19 knockdown in both normoxic and hypoxic conditions The sense primer and antisense primer sequences used in RT-PCR are as follows:

```
Sense primer specific for H19:
                                    (SEQ ID NO: 12)
    5'-CCG GCC TTC CTG AAC A-3';

Antisense primer specific for H19:
                                    (SEQ ID NO: 13)
    5'-TTC CGA TGG TGT CTT TGA TGT-3';

Sense primer specific for GAPDH:
                                    (SEQ ID NO: 14)
    5'-GGC TCT CCA GAA CAT CAT CCC TGC-3';

Antisense primer specific for GAPDH:
                                    (SEQ ID NO: 15)
    5'-GGG TGT CGC TGT TGA AGT CAG AGG-3'.
```

2.4. Enzyme-Linked Immunosorbent Assay (ELISA) Analyses of Proteins that are Affected by H19 Knockdown ELISA analyses are performed on the FLS cells transfected with H19 siRNAs by using commercially appropriate kits. In some experiments, after 24 and 48 hrs of transfection FLS are treated with TNF-α (Sigma Chem. Co., USA) in a concentration of 50 ng/ml and cultured for 1 hr. ELISA analyses are performed by following each kit's instructions.

Example 3

Preparation of Modified H19 siRNAs and Evaluation of their Effects 3.1. Preparation of Modified H19 siRNAs Variants of H19 siRNAs represented by SEQ ID NOs: 5-8 are prepared as detailed in Example 1, with the exception of using nucleosides with 2'-O-methyl and/or phosphorothioate substituents (Dharmacon, Lafayette, Colo., USA).

3.2. Inhibition of Expressions of H19 and Downstream Effectors mRNA by Modified siRNAs The effect of the modified siRNAs on gene expression is evaluated in Hep3B cells and FLS, as detailed in example 2, and compared to that of non-modified siRNAs.

Hep3B cells are obtained from American Type Culture Collection (ATCC). The cells are maintained in DMEM-F12 (1:1) medium supplemented with 10% fetal calf serum (inactivated at 55° C. for 30 min), 25 mM HEPES (pH 7.4), penicillin (180 units/ml), streptomycin (100 µg/ml) and amphotericin B (0.2 µg/ml). Every 4 days, the cells are trypsinized with 0.05% trypsin-EDTA solution (Beit Haemek, Israel) for 10 min and re-plated again using the same initial densities.

3.3. Comparison of the Stabilities of Non-Modified- and Modified-1119 siRNAs in Blood Blood sample are collected from healthy people, left to stand at room temperature for 3 hrs, and centrifuged at 3000 rpm for 15 min to obtain serum as a supernatant. To 90 µl of a solution containing serum (10% (v/v)) and water treated with diethylpyrocarbonate (DEPC), an RNase inhibitor, are added 9 µg of the tested siRNA (described in Examples 1 and 4.1). The samples are incubated at 37° C. for 72 hrs. After 0, 1, 3, 6, 24, 48 and 72 hrs of incubation, the solutions are aliquoted, snap frozen and stored at −70° C. 2.5 µl of each sample is then applied to 12% SDS-PAGE to examine the serum stability of each siRNA.

3.4. Effects of Modified H19 siRNAs on the Suppression of Immune Response.

The in vivo immunogenicity of non-modified-siRNA or modified siRNAs is examined as follows. siRNAs as described in Example 1 and modified siRNAs prepared in Example 3.1 are admixed with liposomes to obtain siRNA/liposome complexes, and injected intravenously to caudal vein of a mouse. The level of interferon-α (IFN-α) in blood serum is measured using an ELISA kit (Quantikine mouse IFN-α kit, R&D Systems, USA) containing an antibody for IFN-α at a range of timescales.

Example 4

Therapeutic Effects of H19 siRNAs in Rheumatoid Arthritis Models 4.1. Cell Proliferation Analysis FLS cells are seeded and transfected in 12 well plates with anti-GFP siRNA or H19 siRNA (modified or non-modified). Twenty four hours later, cells are washed twice with PBS, trypsinized and counted. $5 \times 10^3$ transfected FLS cells are seeded in quadruples in 96 well plates in DMEM media containing 10% FCS, and further incubated for 24 hours before the MTS assay is performed. The MTS assay is performed according to the procedure provided by the supplier (Promega, USA). The absorbance at 940 nm is recorded using ELISA plate reader.

4.2. Measuring the Level of FLS Cell Death after Treatment with H19 siRNAs

The death of FLS cells transfected with H19 siRNA (Examples 1 and 4.1) are examined. In some experiments, siRNAs corresponding to SEQ ID NOs: 4 or 6, or their chemically modified counterparts, are examined. Cells are cultured as detailed in 4.1. In some experiments, the cells are further incubated with of TNF-α.

Cells are examined with a light microscope. Each of the said transfected FLS cells is treated with a fluorescent dye, Annexin V conjugated with Alexa 568 (Roche Applied Science, GB). In the experiments where of TNF-α is added, annexin treatment is performed after 4 hrs from the addition of TNF-α. The cells are then examined with a fluorescent microscope.

Since normal FLS cells and dead FLS cells have filamentous forms and spherical forms, respectively, microscopic examination of cell structure can be used to determine whether the FLS cells are dead or viable. Annexin V is a ligand which can bind phosphatidyl serine in the cellular membrane. Annexin V cannot bind phosphatidyl serine in normal cells, in which it is located within the inner side of cellular membrane. However, if a dead cell whose cellular membrane is destructed is treated with Annexin V bound with Alexa 568, Annexin V binds phosphatidyl serine exposed to outer side of cell.

Example 5

Therapeutic Effects of H19 siRNAs in an In Vivo Model of Rheumatoid Arthritis Collagen-induced arthritis (CIA) is an extensively studied animal model of rheumatoid arthritis (RA). CIA shares both immunological and pathological features of human RA. CIA is primarily an autoimmune disease of joints, requiring both T and B cell immunity to autologous type II collagen (CII) for disease manifestation. This model is reproducible in genetically susceptible strains of mice with MHC haplotypes H-2q or H-2r by immunization with heterologous type II collagen in complete Freund's adjuvant (CFA). Susceptible strains are DBA/1, B10.Q, and B10.RIII.

In some experiments, arthritis is induced in 8-12 week old DBA/1 male mice by injection of 50 μg of chick type II collagen (CII) in CFA on day 0 at the base of the tail (100 μl volume). Animals are boosted on day 21 with 50 μg of CII in incomplete Freund's adjuvant (100 μl volume). Animals are evaluated for 8 weeks.

The mice are administered an siRNA agent targeting H19 or a negative control siRNA (targeting luciferase) in combination with in vivo jetPEI™ (Qbiogene), according to the manufacturer's instructions. Administration is initiated on day 20 post collagen injection and continued daily until final evaluation on day 56.

Animals are evaluated several times each week for signs of arthritis. Any animal with paw redness or swelling is counted as arthritic. Scoring of severity is carried out using a score of 1-3 for each paw (maximal score of 12/mouse). Animals displaying any redness or swelling of digits or the paw are scored as 1. Gross swelling of the whole paw or deformity is scored as 2. Ankylosis of joints is scored as 3.

REFERENCES

Ausubel, et al., Current Protocols in Molecular Biology, John Wiley and Sons, Baltimore, Md., 1989.
Ayesh et al., Mol Carcinog 35, 63-74, 2002.
Berteaux et al., J Biol. Chem. 280(33):29625-36, 2005.
Brantl, Biochem. Biophys. Act. 1575:15-25, 2002.
Chang et al., Somatic Gene Therapy, CRC Press, Ann Arbor, Mich., 1995.
Cullen, Nat. Immunol. 3:597-599, 2002.
Englisch et al., "Angewandte Chemie," International Edition, 30, 613, 1991.
Fingl, et al., 1975, in "The Pharmacological Basis of Therapeutics", Ch. 1 p.1.
Gilboa et al., Biotechniques 4 (6): 504-512, 1986.
Khachigian, L M, Curr Opin Mol Ther 4:119-21, 2002.
Kroschwitz, J. I., ed., "The Concise Encyclopedia Of Polymer Science And Engineering," pages 858-859, John Wiley & Sons, 1990.
Latin et al., Oncogene. Feb. 28; 21(10):1625-31, 2002.
Matouk et al., PLoS One e845, 2007.
Perbal, B., "A Practical Guide to Molecular Cloning," John Wiley & Sons, New York, 1988.
Sambrook et al., Molecular Cloning: A Laboratory Manual, Cold Springs Harbor Laboratory, New York, 2001.
Sanghvi, Y. S., "Antisense Research and Applications," Chapter 15, S. T. Crooke and B. Lebleu, eds., CRC Press, 1993.
Seidman and Glazer, J Clin Invest; 112:487-94, 2003.
Stuhlmuller et al., Am J Pathol. 163(3):901-11, 2003.
Tonkinson et al., Cancer Investigation, 14(1): 54-65, 1996.
Tuschl, ChemBiochem. 2:239-245, 2001.
Vega et al., Gene Targeting, CRC Press, Ann Arbor Mich., 1995.
Vuyisich and Beal, Nuc. Acids Res 28:2369-74, 2000.
Welch et al., Curr Opin Biotechnol. 9:486-96, 1998.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating or inhibiting the progression of rheumatoid arthritis in a subject in need thereof, comprising administering to the subject a therapeutically effective amount of (i) at least one H19-silencing oligonucleotide having a nucleic acid sequence as set forth in any one of SEQ ID NOS: 1-8 and 16-27; or (ii) a recombinant construct comprising at least one nucleic acid sequence encoding a H19-silencing oligonucleotide having a nucleic acid sequence as set forth in any one of SEQ ID NOS: 1-8 and 16-27, wherein the at least one nucleic acid sequence is operably linked to at least one transcription regulating sequence.

2. The method of claim 1, wherein the symptoms of rheumatoid arthritis in the subject is ameliorated or inhibited.

3. The method of claim 1, wherein the at least one H19-silencing oligonucleotide is a small interfering RNA (siRNA) molecule.

4. The method of claim 3, wherein the H19-silencing oligonucleotide comprises a nucleic acid sequence as set forth in SEQ ID NO: 7 or a recombinant construct comprising at least one nucleic acid sequence encoding a H19-silencing oligonucleotide having a nucleic acid sequence as set forth in SEQ ID NO: 7.

5. The method of claim 4, wherein the siRNA molecule comprises a sense RNA strand and an antisense RNA strand, wherein the sense and the antisense RNA strands form an RNA duplex, and wherein at least one strand optionally comprises a 3' overhang.

6. The method of claim 5, wherein the overhang is about 1-5 nucleotides in length.

7. The method of claim 6, wherein the overhang is 2 nucleotides in length.

8. The method of claim 3, wherein said siRNA molecule comprises a sense strand selected from the group consisting of SEQ ID NOS: 5-8.

9. The method of claim 4, wherein said siRNA molecule comprises at least one modified internucleoside linkage.

10. The method of claim 9, wherein the modified internucleoside linkage is a phosphorothioate linkage.

11. The method of claim 4, wherein said siRNA molecule comprises at least one 2'-sugar modification.

12. The method of claim 11, wherein the 2'-sugar modification is a 2'-O-methyl modification.

13. The method claim 1, wherein the at least one H19-silencing oligonucleotide or the recombinant construct is administered to said subject in the form of a pharmaceutical composition further comprising a pharmaceutically acceptable carrier, excipient or diluent.

14. A method for specifically reducing H19 expression in synovial tissue of a subject afflicted with rheumatoid arthritis, comprising administering to the subject a therapeutically effective amount of (i) at least one H19-silencing oligonucleotide having a nucleic acid sequence as set forth in any one of SEQ ID NOS: 1-8 and 16-27; or (ii) a recombinant construct comprising at least one nucleic acid sequence encoding a H19-silencing oligonucleotide having a nucleic acid sequence as set forth in any one of SEQ ID NOS: 1-8 and 16-27, wherein the at least one nucleic acid sequence is operably linked to at least one transcription regulating sequence.

15. The method of claim 14, wherein the at least one H19-silencing oligonucleotide is a small interference RNA (siRNA) molecule.

16. The method of claim 15, wherein the siRNA molecule comprises a sense RNA strand and an antisense RNA strand wherein the sense and the antisense RNA strands form an RNA duplex, and wherein at least one strand optionally comprises a 3' overhang.

17. The method of claim 16, wherein said siRNA molecule comprises a sense strand selected from the group consisting of SEQ ID NOS: 5-8.

18. The method of claim 17, wherein said siRNA molecule comprises at least one modified internucleoside linkage and/or at least one 2'-sugar modification.

19. The method of claim 18, wherein the modified internucleoside linkage is a phosphorothioate linkage.

20. The method of claim 19, wherein the 2'-sugar modification is a 2'-O-methyl modification.

21. The method claim 14, wherein the at least one H19-silencing oligonucleotide is administered to said subject in the form of a pharmaceutical composition further comprising a pharmaceutically acceptable carrier, excipient or diluent.

* * * * *